United States Patent
Treskow et al.

(10) Patent No.: US 11,952,336 B2
(45) Date of Patent: Apr. 9, 2024

(54) PROCESS FOR SEPARATION OF METHANOL AND METHYL (METH)ACRYLATE

(71) Applicant: Evonik Operations GmbH, Essen (DE)

(72) Inventors: Marcel Treskow, Darmstadt (DE); Jerald Andrew Jones, Mobile, AL (US); Marc Becker, Dortmund (DE); Zoe Zegers, Mobile, AL (US); Kevin Lackey, Daphne, AL (US); Ghanem Sabeeh, Richmond, TX (US); Alexander May, Seeheim-Jugenheim (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 18/546,583

(22) PCT Filed: Feb. 7, 2022

(86) PCT No.: PCT/EP2022/052808
§ 371 (c)(1),
(2) Date: Aug. 15, 2023

(87) PCT Pub. No.: WO2022/175122
PCT Pub. Date: Aug. 25, 2022

(65) Prior Publication Data
US 2024/0034711 A1   Feb. 1, 2024

(30) Foreign Application Priority Data
Feb. 17, 2021   (EP) ..................................... 21157515

(51) Int. Cl.
| | | |
|---|---|---|
| *C07C 67/02* | (2006.01) | |
| *B01D 3/00* | (2006.01) | |
| *B01D 3/40* | (2006.01) | |
| *B01J 31/16* | (2006.01) | |
| *C07C 29/84* | (2006.01) | |
| *C07C 67/54* | (2006.01) | |

(52) U.S. Cl.
CPC .............. *C07C 67/02* (2013.01); *B01D 3/009* (2013.01); *B01D 3/40* (2013.01); *B01J 31/1616* (2013.01); *C07C 29/84* (2013.01); *C07C 67/54* (2013.01); *B01J 2231/49* (2013.01); *B01J 2531/46* (2013.01)

(58) Field of Classification Search
CPC ......... C07C 67/02; C07C 29/84; C07C 67/54; B01D 3/009; B01D 3/40; B01J 31/1616; B01J 2231/49; B01J 2531/46
See application file for complete search history.

(56) References Cited

U.S. PATENT DOCUMENTS

| | | |
|---|---|---|
| 4,645,570 A | 2/1987 | Sridhar et al. |
| 4,937,302 A | 6/1990 | Schoedel |
| 6,977,310 B2 | 12/2005 | Ackermann et al. |
| 7,157,610 B2 | 1/2007 | Hofen et al. |
| 8,350,081 B2 | 1/2013 | Balduf |
| 8,829,235 B2 | 9/2014 | Balduf |
| 9,963,417 B2 | 5/2018 | Krill et al. |
| 2005/0119500 A1 | 6/2005 | Ackermann et al. |
| 2006/0135826 A1 | 6/2006 | Hofen et al. |
| 2010/0130648 A1 | 5/2010 | Balduf |
| 2010/0144931 A1 | 6/2010 | Balduf |
| 2016/0090348 A1 | 3/2016 | Misske et al. |
| 2016/0280628 A1 | 9/2016 | Krill et al. |

FOREIGN PATENT DOCUMENTS

| | | |
|---|---|---|
| WO | 2016/069198 | 5/2016 |

OTHER PUBLICATIONS

International Search Report received for PCT Application No. PCT/EP2022/052808, dated Jun. 21, 2022, 3 pages.
Written Opinion received for PCT Application No. PCT/EP2022/052808, dated Jun. 21, 2022, 5 pages.
Extended European Search Report dated Jul. 26, 2021, in European Application No. 21157515.4, 5 pages.

*Primary Examiner* — Deborah D Carr
(74) *Attorney, Agent, or Firm* — Grüneberg and Myers PLLC

(57) ABSTRACT

A process can be used for producing a distillate product with a methanol concentration greater than the concentration of methanol in the minimum boiling azeotrope of methanol and methyl (meth)acrylate, from a mixture with a methanol concentration less than the concentration of methanol in the minimum boiling azeotrope of methanol and methyl (meth) acrylate, in a distillation column. A transesterification process for preparing $C_6$- to $C_{22}$-alkyl, aryl or alkenyl (meth) acrylates from methyl (meth)acrylate is also provided.

20 Claims, No Drawings

PROCESS FOR SEPARATION OF METHANOL AND METHYL (METH)ACRYLATE

CROSS-REFERENCE TO RELATED APPLICATIONS

This application is the National Stage entry under § 371 of International Application No. PCT/EP2022/052808, filed on Feb. 7, 2022, and which claims the benefit of priority to European Application No. 21157515.4, filed on Feb. 17, 2021 The content of each of these applications is hereby incorporated by reference in its entirety.

BACKGROUND OF THE INVENTION

Field of the Invention

The present invention pertains to a process for breaking an azeotrope of methanol and methyl (meth)acrylate and, in addition, provides a transesterification process for preparing $C_6$- to $C_{22}$-alkyl, aryl or alkenyl (meth)acrylates from methyl (meth)acrylate.

The term "breaking an azeotrope of methanol and methyl (meth)acrylate" as used in the context of the present invention refers to a method of producing a distillate product with a methanol concentration greater than the concentration of methanol in the minimum boiling azeotrope of methanol and methyl (meth)acrylate from a mixture with a methanol concentration less than or equal to the concentration of methanol in the minimum boiling azeotrope of methanol and methyl (meth)acrylate in a distillation column.

Description of Related Art

Alkyl, aryl or alkenyl (meth)acrylates are commonly produced by transesterification of methyl (meth)acrylate with the respective alcohol.

The transesterification of methyl (meth)acrylate with an alcohol produces methanol which is usually recovered in the form of a mixture of methanol and methyl (meth)acrylate via distillation. The resulting distillate can have a methanol concentration as high as the azeotropic composition but it is typically lower than this maximum. This leads to undesirable losses of methyl (meth)acrylate. The thus-obtained distillate must be subjected to further processing steps in order to isolate and re-use the methyl (meth)acrylate. For economic reasons, it would be particularly desirable if the impact of azeotrope formation could be mitigated, resulting in decreased losses of methyl (meth)acrylate in the distillate product.

SUMMARY OF THE INVENTION

In view of the above, it was the objective of the present invention to provide a process for breaking a methanol/methyl(meth)acrylate azeotrope either as a process independent from any transesterification reaction or as part of an improved process for preparing alkyl, aryl or alkenyl (meth)acrylates via transesterification, respectively, in which the amount of methyl (meth)acrylate in the distillate is significantly reduced so that the effort for further separation steps as currently required for the distillate could be reduced or even avoided.

For alkyl, aryl or alkenyl (meth)acrylates with linear or branched, acyclic or cyclic alkyl, aryl or alkenyl radical having 6 to 22 carbon atoms, this objective is solved by the process according to the present invention.

The inventors have unexpectedly found that if the azeotrope is treated with a feed of the respective $C_6$- to $C_{22}$-alcohol via the distillation column, the methanol concentration in the distillate can exceed the azeotropic concentration of methanol (i.e. the azeotrope gets broken) and the methyl (meth)acrylate is depleted in the distillate stream and is enriched in the $C_6$- to $C_{22}$-alcohol stream instead. As a result, the methanol concentration in the distillate rises sharply and reaches methyl (meth)acrylate concentrations significantly lower than the azeotropic concentration of methyl (meth)acrylate. Thereby, the efficiency of the process with respect to methyl (meth)acrylate yield is significantly increased.

Accordingly, the present invention provides a process for breaking an azeotrope of methanol and methyl (meth)acrylate, i.e. a process for producing a distillate product with a methanol concentration greater than the concentration of methanol in the minimum boiling azeotrope of methanol and methyl (meth)acrylate from a mixture of methanol and methyl (meth)acrylate with a methanol concentration less than or equal to the concentration of methanol in the minimum boiling azeotrope of methanol and methyl (meth)acrylate in a distillation column, wherein the process comprises a step of contacting a mixture of methanol and methyl (meth)acrylate with a methanol concentration less than or equal to the concentration of methanol in the minimum boiling azeotrope of methanol and methyl (meth)acrylate with an alcohol of formula (I)

$$HO-R^1 \qquad (I),$$

in which $R^1$ is a linear or branched, acyclic or cyclic alkyl, aryl or alkenyl radical having 6 to 22 carbon atoms, that is added via an alcohol feed located at the distillation column.

Further, the present invention pertains to a process for preparing (meth)acrylates of formula (II)

$$CH_2=C(R^2)-CO-OR^1 \qquad (II)$$

in which $R^2$ is hydrogen or methyl and
$R^1$ is a linear or branched, acyclic or cyclic alkyl, aryl or alkenyl radical having 6 to 22 carbon atoms,
by reacting a methyl (meth)acrylate of formula (III)

$$CH_2=C(R^2)-CO-OMe \qquad (III)$$

in which $R^2$ is defined as above,
with an alcohol of formula (I)

$$HO-R^1 \qquad (I)$$

in which $R^1$ is defined as above;
wherein the methanol produced by the transesterification reaction is separated with the methyl (meth)acrylate of formula (III) at a methanol concentration less than or equal to the azeotropic composition of methanol and methyl (meth)acrylate of formula (III) using a distillation column; and the thus-obtained mixture is enriched to a methanol concentration greater than the concentration of methanol in the azeotropic composition of methanol and methyl (meth)acrylate of formula (III) by adding further alcohol of formula (I) via an alcohol feed located at the distillation column.

The processes according to the present invention can be performed batchwise, or, alternatively, in continuous manner.

DETAILED DESCRIPTION OF THE INVENTION

The distillation columns used in the processes of the present invention are preferably extractive distillation columns. Extractive distillation columns may, in addition to its extractive section, further comprise a rectification section and/or a stripping section.

In one embodiment of the present invention, the extractive distillation column is divided into three sections: (1) a rectification section between the top of the column and the alcohol feed location, (2) an extractive section between the alcohol feed location and the azeotrope feed location, and (3) a stripping section located below the azeotrope feed location.

In a different embodiment of the present invention, the extractive distillation column has two sections: (1) a rectification section between the top of the column and the alcohol feed location and (2) an extractive section between the alcohol feed location and the azeotrope feed location.

In the processes according to the present invention, the alcohol feed is located at the distillation column, for example at the top at the distillation column, or, alternatively in the top area of the distillation column.

Preferably, the alcohol feed is located in the top area of the distillation column. As used in the context of the present invention, the term "top area of the distillation column" refers to a position in the extractive distillation column, in which the number of separating trays in the extractive section is greater than or equal to the number of separating trays in the rectification section.

However, feeding the alcohol to the top of the column may result in losses of the alcohol used as the extractive agent. Thus, the alcohol is advantageously fed near the top of the distillation column (i.e in the top area, see above) so that the separation capability of the extractive section is maximized while providing sufficient rectification to avoid excessive alcohol losses. In other words, the preferred position of the alcohol feed is such that enough column height for extraction is given.

Preferably, above the alcohol feed, there is a minimum of 0.01 and, in order to avoid undesired enrichment back toward the azeotropic composition, a maximum of 10 theoretical separation trays.

The alcohol of formula (I) may, for example, be added via the alcohol feed at a temperature between 0° C. and 70° C.

The addition of the alcohol of formula (I) via the distillation column may be performed batchwise or continuously.

To prevent undesirable polymerization of the (meth) acrylates, polymerization inhibitors can be used in the processes according to the present invention. Advantageously, these processes are performed in the presence of an inhibitor composition comprising or consisting of at least one phenolic polymerization inhibitor.

These compounds, for example hydroquinones, hydroquinone ethers such as hydroquinone monomethyl ether or di-tert-butylcatechol, phenothiazine, N,N'-(diphenyl)-p-phenylenediamine, 4-hydroxy-2,2,6,6-tetramethylpiperidin-1-oxyl, p-phenylenediamine, methylene blue or sterically hindered phenols, are widely known in the art. These compounds can be used individually or in the form of mixtures and are generally commercially available. The mode of action of the stabilizers is usually that they act as free-radical scavengers for the free radicals occurring in the polymerization. Based on the weight of the total reaction mixture, the proportion of inhibitors, either individually or as a mixture, can generally be 0.001-0.5% (wt/wt).

These polymerization inhibitors can be added before or at the beginning of the reaction or distillation, respectively. Furthermore, small proportions of the polymerization inhibitors employed can be introduced during the transesterification. Processes in which part of the polymerization inhibitor is added via the column reflux are of particular interest here. It is particularly advantageous to use, inter alia, mixtures containing methyl (meth)acrylate, hydroquinone monomethyl ether and 4-hydroxy-2,2,6,6-tetramethylpiperidin-1-oxyl. This measure makes it possible, in particular, to avoid undesirable polymerization within the distillation column.

Furthermore, gaseous oxygen can be used for the inhibition. This can be used, for example, in the form of air, with the amounts introduced advantageously being such that the content in the gas phase above the reaction mixture remains below the limiting oxygen concentration of the explosive region. Amounts of air in the range from 0.05 to 0.5 l per hour and mol of the primary alcohol are particularly preferred. It is likewise possible to use inert gas/oxygen mixtures, e.g. nitrogen/oxygen or argon/oxygen mixtures.

In a particular embodiment of the present invention, a combination of oxygen with hydroquinone monomethyl ether (HQME) can be used for inhibition.

Alternatively, the processes according to the present invention may be performed in the presence of an inhibitor composition comprising or consisting of a polymerization inhibitor selected from the group consisting of 4-hydroxy-2,2,6,6-tetramethylpiperidinel-oxyl, 2,2-diphenyl-1-picrylhydrazyl, phenothiazine, N, N'-diphenyl-p-phenylenediamine, nigrosine, para-benzoquinone, and cupferron, optionally in combination with a phenolic polymerization inhibitor.

Within the context of the present invention, the term "alkyl, aryl or alkenyl (meth)acrylate" is understood to mean alkyl, aryl or alkenyl esters both of methacrylic acid and of acrylic acid.

In the alkyl, aryl or alkenyl (meth)acrylates of formula (II) and in the alcohol of formula (I), respectively, $R^1$ may be selected from linear or branched, acyclic or cyclic alkyl, aryl or alkenyl radicals having 6 to 22 carbon atoms. The term "cyclic alkyl radical" refers to mono- or multicyclic alkyl species, and thus includes bicyclic radicals such as isobornyl. Preferably, $R^1$ is a linear or branched, acyclic or cyclic alkyl, aryl or alkenyl radical having 7 to 20, advantageously 8 to 18 carbon atoms.

The $R^1$ radical is understood, for example, to mean a n-hexyl, n-heptyl, n-octyl, n-nonyl, n-decyl, n-undecyl, n-dodecyl, 2-octyl, 2-ethylhexyl, nonyl, 2-methyloctyl, 2-tert-butylheptyl, 3-isopropylheptyl, decyl, undecyl, 5-methylundecyl, dodecyl, stearyl and/or behenyl radical, and/or a cycloalkyl radical such as cyclohexyl, tert-butylcyclohexyl, cycloheptyl, cyclooctyl, bornyl and/or isobornyl. Moreover, the $R^1$ radical may be an optionally substituted $(C_6-C_{14})$-aryl-$(C_1-C_8)$-alkyl radical, preferably a $(C_6-C_{12})$-aryl-$(C_1-C_4)$-alkyl radical, for example the benzyl, naphthylmethyl, naphthylethyl, 2-phenylethyl, 2-phenoxyethyl, 4-phenylbutyl, 3-phenylbutyl, 2-phenylbutyl and/or the 2-biphenylethyl radical.

The methyl (meth)acrylate of formula (III) may be introduced into the transesterification process according to the present invention as a pure substance or, for example, as a mixture containing a methanol concentration less than or equal to the azeotrope composition (from a previous reaction), or as a combination of fresh/pure methyl (meth) acrylate of formula (III) with a mixture of methyl (meth) acrylate of formula (III) with methanol, said mixture having a methanol concentration less than or equal to the azeotropic composition of methanol and methyl (meth)acrylate of formula (III). Such process setting is particularly suitable for transesterification processes carried out in continuous manner.

The process according to the present invention may, for example, also be realized at a standalone plant. An arbitrary alcohol (i.e. the alcohol of formula (I)) that is not forming an azeotrope with the (meth)acrylate of formula (III), is added via a first column to break the azeotrope. Then, in a second column, the methyl (meth)acrylate of formula (III) is separated from the alcohol of formula (I) and said alcohol is then reused in the first column.

In a batch process, the azeotrope may be fed to the reactor prior to the alcohol and kept boiling under full reflux. Then, the alcohol desired for the reaction is fed into the column. While this alcohol is extracting the methyl (meth)acrylate of formula (III) out of the boiling azeotrope, it is also starting the transesterification reaction.

In a particularly preferred embodiment of the present invention, the (meth)acrylate of formula (II) is 2-ethylhexyl methacrylate, the methyl (meth)acrylate of formula (III) is methyl methacrylate and the alcohol of formula (I) is 2-ethylhexanol.

The molar ratio of the alcohol of the formula (I) to the (meth)acrylate of the formula (III) fed to the transesterification reactor is preferably in the range of 10:1 to 1:10, more preferably 1:1 to 1:5 and most preferably in the range of 1:1.1 to 1:2.5. The latter ratios are particularly suitable for continuous transesterification processes.

In a preferred embodiment of the present invention, after an initial reaction period, the further amounts (or the remaining equivalents) of alcohol (I) are introduced into the reaction mixture via the distillation column in order to enrich the methanol to a concentration greater than the methanol concentration in the azeotrope The addition of alcohol (I) via the distillation column may be initiated directly after starting the transesterification, or, alternatively, after the reaction has reached a steady state. In a batch process, the alcohol feed to the distillation column may be initiated at the beginning of the batch or at some point later in the batch.

To catalyze the present transesterification, it is possible to use catalysts selected from the group consisting of alkyl titanates (e.g. tetraisopropyl titanate, tetrakis(ethylhexyl) titanate), zirconium acetylacetonate, dialkyltin compounds, lithium compounds (e.g. lithium oxide, lithium hydroxide, lithium chloride, lithium amide ($LiNH_2$), lithium alcoholates (preferably LiOMe), calcium compounds (e.g. calcium oxide and calcium hydroxide), or acids (e.g. p-toluenesulphonic acid, sulphuric acid, methanesulphonic acid), alone or in any combination of the aforementioned catalysts.

Particularly suitable catalysts are e.g. tetraisopropyl titanate, tetrakis (ethylhexyl) titanate, and zirconium acetylacetonate. The catalyst may be purchased in ready-to-use form or may be prepared in situ. Alternatively, the catalyst may be obtained via recycling from downstream processing.

Advantageously, it is possible to use 0.2 to 10 mmol, more preferably 0.5 to 8 mmol, of catalyst per mole of alcohol of the formula (I).

The reaction times depend inter alia on the parameters selected, for example pressure and temperature. However, they are generally in the range from 1 to 24 hours, preferably from 5 to 20 hours and very particularly preferably from 6 to 18 hours. In the case of continuous processes, the reactor residence times are generally in the range from 1 to 24 hours, preferably from 2 to 20 hours and very particularly preferably from 2.5 to 10 hours.

The reaction can preferably take place upon stirring, with the stirring rate particularly preferably being in the range from 50 to 2000 rpm, very particularly preferably in the range from 100 to 500 rpm.

A suitable plant for performing the present transesterification may, for example, be a stirred tank reactor with a stirrer, steam heater, distillation column (azeotrope column) and condenser. The size of the plant depends on the amount of alkyl (meth)acrylate to be prepared, and the process according to the invention can be performed either on the laboratory scale (reactor volume 0.5-20 litres) or, particularly advantageously, on the industrial scale. In a particular aspect, the stirred tank reactor may accordingly have a tank volume in the range of 0.25 $m^3$ to 50 $m^3$, preferably 1 $m^3$ to 50 $m^3$, more preferably 3 $m^3$ to 25 $m^3$. The stirrer of the reactor tank can be configured especially in the form of an anchor stirrer, impeller, paddle stirrer or INTERMIG® stirrer.

The distillation column (azeotrope column) may have one, two or more separating stages. The number of separating stages refers to the number of trays in a tray column or the number of theoretical plates in the case of a column with structured packing or a column with random packing.

Examples of a multistage distillation column with trays include those such as bubble-cap trays, sieve trays, tunnelcap trays, valve trays, slot trays, slotted sieve trays, bubble-cap sieve trays, jet trays, centrifugal trays.

Examples of a multistage distillation column with random packings are those such as Raschig rings, Raschig Super Rings, Lessing rings, Pall rings, Berl saddles, Intalox saddles; and examples of a multistage rectification column with structured packings are those such as the Mellapak type (Sulzer), MellapakPlus, the Rombopak type (Kühni), the Montz-Pak type (Montz). Preferably, above the alcohol feed, there is a minimum of 0.01 and, in order to avoid undesired enrichment back toward the azeotropic composition, a maximum of 10 theoretical separation trays.

The use of distillation columns having combination of different internals is also possible, such as, for example a structured packing in a first column section and trays or random packs in a second column section.

After the reaction has ended, the resulting alkyl (meth) acrylate in many cases already satisfies the general requirements of the respective alkyl (meth)acrylate product, such that further purification is in many cases not necessary. However, the product may also be isolated by distillation after the reaction has ended.

To further enhance the quality and especially to remove the catalyst, the resulting mixture can be purified by known processes. Owing to the polymerization tendency of the monomer, it is advisable to employ distillation processes in which the thermal stress on the substance to be distilled is minimized. Very suitable apparatus is that in which the monomer is evaporated continuously from a thin layer, such as falling-film evaporators and evaporators with a rotating wiper system. Short-path evaporators can also be used. For example, a distillation can be performed, in which a continuous evaporator with a rotating wiper system and attached column can be used. This distillation can be performed, for example, at a pressure in the range of 1 to 60 mbar and an evaporator temperature (surface temperature of wiped film evaporator) of 60° C. to 130° C.

In the following, the invention is illustrated by non-limiting examples and exemplifying embodiments.

EXAMPLES

Comparative Example 1

In a continuous transesterification reaction system consisting of a reactor fitted with an azeotrope column and an additional column for workup of a continuously withdrawn reactor crude product from which the unreacted raw materials are separated and recycled the reactor is continuously supplied with alcohol, MMA and catalyst (titanium (IV) alkoxide). The reactants were introduced to the reactor. In the present example 2-ethylhexanol was used as the alcohol. Methanol produced through reaction conversion is continuously withdrawn from the reactor in the form of a mixture containing methanol at a concentration lower than or equal to the azeotropic concentration of methanol via the azeotrope column. In order to assess concentration during operation, the density of the distillate is measured and recorded in real time and used to calculate the ratio of methanol and MMA (from the temperature corrected densities of the pure substances). As a result of thermodynamic limitations to separation performance due to the azeotrope the concentration at the top of the column is typically 78 wt. % methanol. After attainment of the steady state a sample of the recovered methanol distillate was withdrawn and analyzed. The result is reported in table 1.

Example 1

In a continuous transesterification reaction system consisting of a reactor fitted with an azeotrope column and an additional column for workup of a continuously withdrawn reactor crude product from which the unreacted raw materials are separated and recycled the reactor is continuously supplied with alcohol, MMA and catalyst (titanium (IV) alkoxide). The reactants were introduced to the reactor and the feed point for the alcohol was moved to a location near the top of the azeotrope column without preheating the alcohol. The temperature of the alcohol was 20° C. Arranged above the feed point of the alcohol are structured packing elements having a theoretical separation power of approx. 0.8 trays. In the present example 2-ethylhexanol was used as the alcohol. Methanol produced through reaction conversion is continuously withdrawn from the reactor in the form of a mixture containing methanol at a concentration lower than the azeotropic concentration of methanol via the azeotrope column. In order to assess concentration during operation the density of the distillate is measured and recorded in real time and used to calculate the ratio of methanol and MMA (from the temperature corrected densities of the pure substances). The reactor was started up according to comparative example 1 and after attaining the steady state the feed point for the alcohol was changed as described above. The concentration of methanol in the distillate demonstrably reacts to the changing of the feed points within 2 min, the recovered methanol distillate assuming concentrations of more than 78 wt. % methanol. After half an hour the first sample of the distillate was taken at a calculated concentration of 90 wt. % methanol; the analytical determination is very largely identical. The second sample after 2 h and 93 wt. % calculated purity has an analytical content of 92.7 wt. % methanol and the third sample after 4 h after achieving a steady state of 94.5 wt. % methanol has an analytical content of 93.25 wt. % methanol. In accordance with the enrichment of methanol in the distillate the total amount of withdrawn distillate fell. In accordance with the lower concentration of withdrawn MMA in the azeotrope the feed of MMA into the reactor is reduced after attainment of a steady state. The overhead temperature of the column is unchanged. At the bottom vapor inlet of the column the temperature fell by 20° C. from 94° C. to 74° C. The differential pressure within the column is unchanged.

TABLE 1

| Sample | Sum of MEOH + MMA [wt. %] | MEOH [wt. %] | MMA [wt. %] | 2-EHOH [wt. %] | TOTAL IMPURITIES [wt. %] |
|---|---|---|---|---|---|
| Comparative Example 1 | 99.89 | 77.93 | 21.97 | | 0.04 |
| Example 1, after 1 h | 99.68 | 89.37 | 10.31 | 0.27 | 0.31 |
| Example 1, after 2 h | 99.67 | 92.71 | 6.96 | 0.31 | 0.31 |
| Example 1, after 4 h | 99.69 | 93.25 | 6.44 | 0.28 | 0.28 |

Example 2

In a glass flask, V=3 L, fitted with a stirrer, electric heating mantle and mirrored random-packed column (bottom section height=0.3 m, diameter=45 mm, top section height=0.7 m, diameter=condenser and reflux divider, 1.8 kg of a mixture of 75 wt % of MeOH and 25 wt % of MMA are initially charged. Air is additionally bubbled into the reactor contents at 2 NL/h. The mixture is stabilized with 1000 (by weight) ppm of HQME and 50 ppm (by weight) of Tempol (4-hydroxy-2,2,6,6-tetramethylpiperidin-1-oxyl). A thermocouple for monitoring temperature is placed both in the flask and in the column top. The mixture in the flask is heated to boiling and at the top of the column a reflux:withdrawn distillate ratio of 1:1 was established at the reflux divider. After achieving a stable overhead temperature, the collected distillate is sampled and analyzed by GC.

After a further 15 minutes, 8 g/min of 2-ethylhexanol are added at the top of the column with the reflux using an HPLC pump and a coriolis mass flow meter. The obtained distillate is sampled again and analyzed after 10 min and 45 min. The reflux:withdrawn distillate ratio of 1:1 is left unchanged.

Example 3

Procedure as per example 2 but adding 7 g/min of i-decyl alcohol as the alcohol.

Example 4

Procedure as per example 2 but adding 6 g/min of C13.0 alcohol (Lorol Spezial) as the alcohol.

Example 5

Procedure as per example 2 but adding 7 g/min of cyclohexanol as the alcohol.

Comparative Example 2

Procedure as per example 2 but adding 7.3 g/min of n-BuOH as the alcohol.

The results of the distillate analyses for the experiments are summarized in table 2.

TABLE 2

| | GC distillate analysis [wt %] | | |
|---|---|---|---|
| | MeOH | MMA | corresponding alcohol |
| Reference without alcohol addition | 83.8 | 16.2 | 0 |
| Example 2 | 92.5 | 7.0 | 0.5 |
| Example 3 | 89.75 | 10.2 | 0.05 |
| Example 4 | 89.2 | 10.7 | 0.1 |
| Example 5 | 85.5 | 13.2 | 1.3 |
| Comparative example 2 | 80.2 | 10.3 | 10.5 |

It is apparent that without addition of alcohol at the column top a composition close to the azeotropic composition of MMA and MeOH results (about 85.5 wt. % MeOH and 14.5 wt. % MMA at 1013 mbar), see the reference without alcohol addition.

By contrast, alcohols with sufficiently low polarity (e.g. $C_nH_{2n+1}$—OH, n≥6; $C_nH_{2n-1}$—OH, n≥6 or $C_nH_{2n-7}$—OH, n≥6) having a normal boiling point greater than the normal boiling point of MMA (100° C.) selectively extract the MMA from the mixture of methanol and MMA into the bottom of the column and thus allow the methanol concentration to exceed the azeotropic concentration of methanol and thus a further enrichment of methanol.

By contrast, more polar, short-chain alcohols (comparative example 2) do not produce a distillate product with a methanol concentration greater than the concentration of methanol in the minimum boiling azeotrope of methanol and methyl methacrylate.

The invention claimed is:

1. A process for producing a distillate product with a methanol concentration greater than the concentration of methanol in a minimum boiling azeotrope of methanol and methyl (meth)acrylate, from a mixture of methanol and methyl (meth)acrylate with a methanol concentration less than or equal to the concentration of methanol in the minimum boiling azeotrope of methanol and methyl (meth) acrylate in a distillation column, the process comprising:

contacting a mixture of methanol and methyl (meth) acrylate, with a methanol concentration less than or equal to the concentration of methanol in the minimum boiling azeotrope of methanol and methyl (meth)acrylate, with an alcohol of formula (I)

HO—R$^1$ (I), in which R$^1$ is a linear or branched, acyclic or cyclic alkyl, aryl or alkenyl radical having 6 to 22 carbon atoms, wherein the alcohol of formula (I) is added via an alcohol feed located at the distillation column.

2. The process according to claim 1, wherein the distillation column is an extractive distillation column having at least an extractive section and a rectification section; and the alcohol feed is located therein such that a number of separating trays in the extractive section is greater than or equal to a number of separating trays in the rectification section.

3. The process according to claim 1, wherein above the alcohol feed, there is a minimum of 0.01 and a maximum of 10 theoretical separation trays.

4. The process according to claim 1, wherein the alcohol of formula (I) is added via the alcohol feed at a temperature between 0° C. and 70° C.

5. The process according to claim 1, wherein the process is performed batchwise, or, alternatively, in a continuous manner.

6. A process for preparing a (meth)acrylate of formula (II)

$CH_2$=C(R$^2$)—CO—OR$^1$ (II), in which
R$^2$ is hydrogen or methyl, and
R$^1$ is a linear or branched, acyclic or cyclic alkyl, aryl or alkenyl radical having 6 to 22 carbon atoms,
the process comprising:
reacting a methyl (meth)acrylate of forma (III)

$CH_2$=C(R$^2$)—CO—OMe (III), in which R$^2$ is defined as above,
with an alcohol of formula (I)

HO—R$^1$ (I), in which R$^1$ is defined as above;
wherein the methanol produced by the transesterification reaction is separated with the methyl (meth)acrylate of formula (III) at a methanol concentration less than or equal to an azeotropic composition of methanol and methyl (meth)acrylate of formula (III) using a distillation column; and
a thus-obtained mixture is enriched to a methanol concentration greater than the concentration of methanol in the azeotropic composition of methanol and methyl (meth)acrylate of formula (III), by adding further alcohol of formula (I) via an alcohol feed located at the distillation column.

7. The process according to claim 6, wherein the distillation column is an extractive distillation column having at least an extractive section and a rectification section; and the alcohol feed is located therein such that a number of separating trays in the extractive section is greater than or equal to a number of separating trays in the rectification section,
and/or
wherein above the alcohol feed, there is a minimum of 0.01 and a maximum of 10 theoretical separation trays.

8. The process according to claim 6, wherein the process is performed batchwise, or, alternatively, in a continuous manner.

9. The process according to claim 6, wherein the addition of the alcohol of formula (I) via the distillation column is initiated after the reaction has reached a steady state.

10. The process according to claim 6, wherein the methyl (meth)acrylate of formula (III) is introduced to the transesterification reaction as a mixture of methyl (meth)acrylate of formula (III) with methanol, said mixture having a methanol concentration less than or equal to the azeotropic composition of methanol and methyl (meth)acrylate of formula (III); or, alternatively,
as a combination of methyl (meth)acrylate of formula (III) with a mixture of methyl (meth)acrylate of formula (III) with methanol, said mixture having a methanol concentration less than or equal to the azeotropic composition of methanol and methyl (meth)acrylate of formula (III).

11. The process according to claim 6, wherein in the (meth)acrylate of formula (II) and in the alcohol of formula (I), R$^1$ is a linear or branched, acyclic or cyclic alkyl, aryl or alkenyl radical having 7 to 20 carbon atoms.

12. The process according to claim 6, wherein the (meth) acrylate of formula (II) is 2-ethylhexyl methacrylate, the methyl (meth)acrylate of formula (III) is methyl methacrylate, and the alcohol of formula (I) is 2-ethylhexanol.

13. The process according to claim 6, wherein the alcohol of formula (I) is added at a temperature between 0° C. and 70° C.

14. The process according to claim 6, wherein the transesterification reaction is performed in the presence of a catalyst.

15. The process according to claim 6, wherein the transesterification reaction is performed in the presence of an inhibitor composition comprising at least one phenolic polymerization inhibitor.

16. The process according to claim 10, wherein the mixture is obtained from a previous transesterification reaction involving methanol formation.

17. The process according to claim 11, wherein in the alkyl (meth)acrylate of formula (II) and in the alcohol of formula (I), $R^1$ is a linear or branched, acyclic or cyclic alkyl, aryl or alkenyl radical having 8 to 18 carbon atoms.

18. The process according to claim 14, wherein the catalyst is selected from the group consisting of alkyl inmates, zirconium acetylacetonate, dialkyltin compounds, lithium compounds, calcium compounds, and combinations thereof.

19. The process according to claim 14, wherein the catalyst is present in an amount of 0.2 to 10 mmol per mole of alcohol of the formula (I).

20. The process according to claim 15, wherein the phenolic polymerization inhibitor is hydroquinone, hydroquinone monomethyl ether, or a combination thereof.

* * * * *